United States Patent
Reuter

(10) Patent No.: US 7,566,796 B2
(45) Date of Patent: Jul. 28, 2009

(54) PROCESSES FOR PREPARING NIOBIUM ALKOXIDES, AND NIOBIUM ALKOXIDES PREPARED THEREBY

(75) Inventor: Knud Reuter, Krefeld (DE)

(73) Assignee: H. C. Starck GmbH, Goslar (DE)

( * ) Notice: Subject to any disclaimer, the term of this patent is extended or adjusted under 35 U.S.C. 154(b) by 0 days.

(21) Appl. No.: 11/855,219

(22) Filed: Sep. 14, 2007

(65) Prior Publication Data

US 2008/0071102 A1 Mar. 20, 2008

(30) Foreign Application Priority Data

Sep. 14, 2006 (DE) .................. 10 2006 043 042

(51) Int. Cl.
*C07F 9/00* (2006.01)
(52) U.S. Cl. .................................... 556/42
(58) Field of Classification Search ............ 556/42
See application file for complete search history.

(56) References Cited

U.S. PATENT DOCUMENTS 5,919,963 A * 7/1999 Hochido et al. ............ 556/42

7,273,943 B2 * 9/2007 Reuter et al. .................. 556/42

OTHER PUBLICATIONS

Search results from Deutsches Institut fur Normung e.V. website (http://www.din.de) for the search term DIN 6271 (Sep. 16, 2008).*

* cited by examiner

*Primary Examiner*—Porfirio Nazario Gonzalez
(74) *Attorney, Agent, or Firm*—Connolly Bove Lodge & Hutz LLP

(57) ABSTRACT

Processes for preparing high-purity niobium alkoxides, especially niobium ethoxide, are described which include: (a) providing a crude niobium alkoxide starting material comprising at least one compound of the general formula (I)

$$Nb(OR)_5 \qquad (I)$$

wherein each R independently represents a linear or branched $C_{1-12}$ alkyl group; and (b) contacting the crude niobium alkoxide starting material with a treatment medium comprising a component selected from the group consisting of (i) one or more alcohols of the general formula (II) in an amount of 0.01 to 5% by weight, (ii) air or an oxygen-containing gas, and (iii) combinations thereof;

$$R^1OH \qquad (II)$$

wherein each $R^1$ independently represents a linear or branched $C_{1-12}$ alkyl group.

15 Claims, 1 Drawing Sheet

PROCESSES FOR PREPARING NIOBIUM ALKOXIDES, AND NIOBIUM ALKOXIDES PREPARED THEREBY

BACKGROUND OF THE INVENTION

Niobium alkoxides, frequently also referred to in the literature as niobium alcoholates, can be utilized for the deposition of corresponding metal oxide layers by means of chemical vapor deposition (CVD) and are therefore valuable starting compounds for producing extremely robust components which find use, for example, in the electronics industry. Such metal oxide layers can also be produced from the corresponding niobium alkoxides via hydrolysis using a sol-gel method. The very high dielectric constant enables, for example, the use of niobium oxide layers in DRAMs (Dynamic Random Access Read/Write Memories). Also, in the lamp industry, niobium oxide which can be deposited by CVD methodologies plays a role, for example, for the production of incandescent bulbs.

However, an existing problem for the electronics industry and also for lamp manufacturers relates to the extreme requirements as to the purity of the starting materials for such layers, i.e., the alkoxides.

The most commonly used, technically simple and economically viable preparation of the niobium alkoxides generally proceeds from the corresponding metal(V) chlorides and alcohols. A comprehensive overview is given by the work "Alkoxo and Aryloxo Derivatives of Metals" by D. C. Bradley, R. C. Mehrotra, I. P. Rothwell and A. Singh, Academic Press, 2001, One such procedure is, for example, described in German Patent Publication No. DE 10 113 169 A1.

Despite some significant chemical similarity to the analogous but virtually colorless tantalum alkoxide compounds, niobium alkoxides (especially niobium ethoxide and higher niobium alkoxides), in contrast, can be obtained only with extreme difficulty in a lighter-colored and hence purer form than the highly colored "crude" niobium alkoxide starting materials. In general, even known distilled niobium alkoxide materials are yellow(-orange) to red-brown in color. For example, a Hazen color number of >280 is a typical measurement for commercially sold niobium ethoxide. This is the case even after repeated distillation. In particular, a reliable, reproducible preparation of light-colored or virtually colorless niobium ethoxide has to date not been possible by distillation alone (vacuum distillation; b.p. 153° C./0.1 mmHg or 200° C./5.5 mmHg).

For example, D. C. Bradley, B. N. Chakravarti, W. Wardlaw; J. Chem. Soc. 1956, pp. 2381-2384, refer to niobium ethoxide, niobium n-propoxide and niobium n-butoxide as yellow liquids. Using the example of niobium ethoxide, it is recognized that the yellow color cannot be eliminated via repeated distillations. As a route to a higher-purity, only slightly yellow niobium ethoxide, the following complicated process is described: yellow niobium ethoxide is converted in boiling isopropanol to a crystalline mixture of $Nb(OEt)(O^iPr)_4$ and $Nb(OEt)_2(O^iPr)_3$, which is recrystallized four times. Thereafter, this mixed ethoxide-isopropoxide is treated with ethanol four times. Only the distillation of the niobium ethoxide obtained in this complicated manner is described as giving rise to a higher-purity, only slightly yellow product.

Such a complicated process is unusable for an industrial preparation of high-purity, almost colorless niobium ethoxide or higher niobium alkoxides.

BRIEF SUMMARY OF THE INVENTION

The invention relates to novel processes for preparing high-purity niobium alkoxides, especially niobium ethoxide. The processes of the present invention can provide niobium alkoxides, especially niobium ethoxide, niobium n-propoxide, the isomeric niobium butoxides and the isomeric niobium pentoxides, in surprisingly high-purity, light-colored form via simplified methods which are easy to implement in industry, inexpensive and have very good reproducibility.

The invention includes processes for preparing high-purity light-colored niobium alkoxides of the general formula (I):

$$Nb(OR)_5 \qquad (I)$$

where each R is identical or different, but preferably identical linear or branched $C_1$-$C_{12}$-alkyl, preferably linear or branched $C_1$-$C_6$-alkyl, more preferably methyl, ethyl, n-propyl, isopropyl, n-butyl, isobutyl, 2-butyl, tert-butyl, n-pentyl, 2-pentyl, 3-pentyl, 2-methyl-1-butyl, 2-methyl-2-butyl or 3-methyl-2-butyl;

the processes characterized in that crude niobium alkoxides of the general formula (I) (also referred to herein as "crude niobium alkoxide starting materials") are purified by the addition of 0.01 to 5% by weight, preferably 0.1 to 2% by weight, of one or more alcohols of the general formula (II):

$$R^1OH \qquad (II)$$

where $R^1$, independently of R, is identical or different, but preferably identical, linear or branched $C_1$-$C_{12}$-alkyl, preferably linear or branched $C_1$-$C_6$-alkyl, more preferably methyl ethyl, n-propyl, isopropyl, n-butyl, isobutyl, 2-butyl, tert-butyl, n-pentyl, 2-pentyl, 3-pentyl, 2-methyl-1-butyl, 2-methyl-2-butyl or 3-methyl-2-butyl;

or treatment with air or other oxygenous gas mixtures and optionally subsequent distillation.

One embodiment of the present invention include processes comprising: (a) providing a crude niobium alkoxide starting material comprising at least one compound of the general formula (I)

$$Nb(OR)_5 \qquad (I)$$

wherein each R independently represents a linear or branched $C_{1-12}$ alkyl group; and (b) contacting the crude niobium alkoxide starting material with a treatment medium comprising a component selected from the group consisting of (i) one or more alcohols of the general formula (II) in an amount of 0.01 to 5% by weight, (ii) air or an oxygen-containing gas, and (iii) combinations thereof;

$$R^1OH \qquad (II)$$

wherein each $R^1$ independently represents a linear or branched $C_{1-12}$ alkyl group It may be advantageous, but is not required, that the alcohol $R^1OH$ has the same alkyl radical as the niobium alkoxide of the general formula (I) to be purified. In particularly preferred embodiments, R and $R^1$ therefore have the same definition.

In the context of the invention, crude niobium alkoxides of the general formula (I) are understood to mean those niobium alkoxides of the general formula (I) which are obtained after the synthesis of these niobium alkoxides of the general formula (I), optionally after distillation or optionally even without further purification. Such synthesis processes are sufficiently well known to those skilled in the art and have been described many times in the literature and patent literature; see, for example, in "Alkoxo and Aryloxo Derivatives of Metals" by D. C. Bradley, R. C. Mehrotra, I. P. Rothwell and A. Singh, Academic Press, 2001.

Experience has shown that coloring impurities play a relatively minor role in the case of niobium methoxide, since it is usually obtained in the form of colorless (white) crystals in the case of careful operation. Therefore, in preferred embodiments of the process according to the invention, R and $R^1$ are each independently identical or different, but preferably identical, linear or branched $C_2$- to $C_5$-alkyl radicals, most preferably ethyl, n-propyl, isopropyl, n-butyl, isobutyl, 2-butyl, tert-butyl, n-pentyl, 2-pentyl, 3-pentyl, 2-methyl-1-butyl, 2-methyl-2-butyl or 3-methyl-2-butyl.

BRIEF DESCRIPTION OF THE SEVERAL VIEWS OF THE DRAWING

The foregoing summary, as well as the following detailed description of the invention, will be better understood when read in conjunction with the appended drawings. For the purpose of assisting in the explanation of the invention, referenced in the drawings are representative embodiments which are considered illustrative. It should be understood, however, that the invention is not limited to the precise arrangements and instrumentalities shown or referenced.

In the Figures.

DETAILED DESCRIPTION OF THE INVENTION

Figure 1:
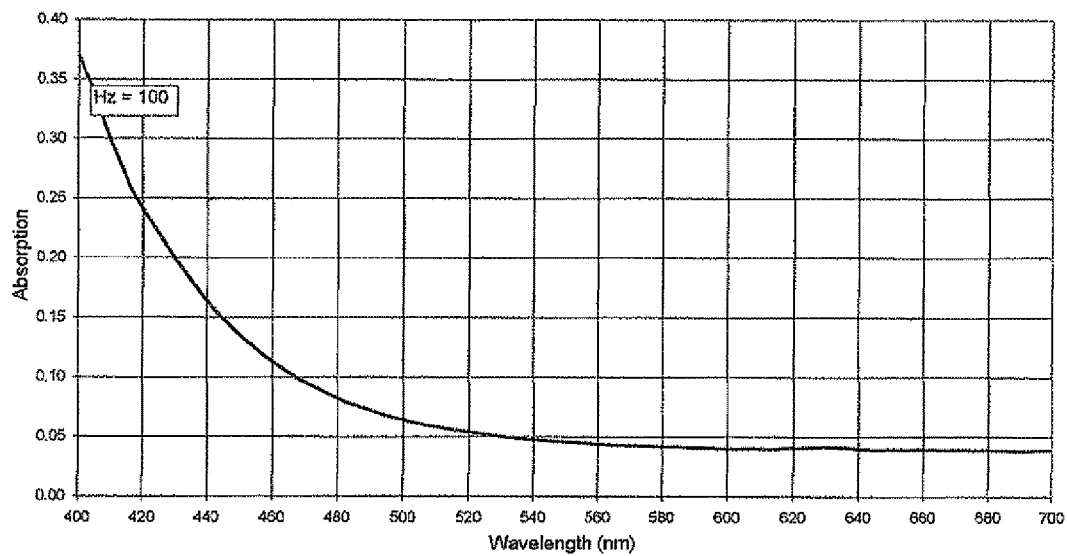
FIG. 1 is a graphical representation of the absorption of a niobium alkoxide prepared in accordance with a process according to one embodiment of the present invention, as a function of wavelength.

As used herein, the singular terms "a" and "the" are synonymous and used interchangeably with "one or more" and "at least one." Accordingly, for example, reference to "a compound" herein or in the appended claims can refer to a single compound or more than one compound. Additionally, all numerical values, unless otherwise specifically noted, are understood to be modified by the word "about."

In very particularly preferred embodiments of the processes according to the invention, the niobium alkoxide of the general formula (I) is niobium ethoxide and the alcohol of the general formula (II) is ethanol.

The oxygenous gas mixtures (also referred to herein as "oxygen-containing gas(es)" are preferably those which, as well as oxygen, comprise essentially inert components, for example noble gases—for example argon—and/or nitrogen, which, to prevent the hydrolysis of the niobium alkoxide, should be dry. Particular preference is given to treating with dry air or a dry oxygen-argon gas mixture.

In the context of the present invention, dry is understood to mean air or oxygen-containing gas mixtures which do not bring about any significant hydrolysis of the niobium alkoxides to be purified. Dry is preferably understood to mean a water content corresponding to a water vapor pressure at 20° C. of <0.25 cPa, especially <0.05 kPa.

When insufficiently dried air or a not entirely dry oxygenous gas mixture is used in a process according to the invention, the desired purification effect is nevertheless achieved. At the same time, the moisture present hydrolyzes the niobium alkoxide of the general formula (I) to alcohol ROH and niobium oxide. The alcohol formed, in addition to the oxygen present, can provide the desired purification effect of the processes according to the invention. However, this procedure is not preferred, since the amount of alcohol formed can be regulated and controlled only very poorly and, moreover, the niobium oxide formed precipitates out, is therefore lost and additionally has to be removed again in a complicated manner, for example by filtration.

Preference is accordingly given to the treatment of the crude niobium alkoxides of the general formula (I) with dry air or a dry oxygenous mixture. For reasons of cost, particular preference is given to treatment with dry air.

Dry air or a dry gas mixture, for example oxygen-protective gas (argon) mixture, is provided in the manner known to those skilled in the art by passing it through liquid desiccants or preferably passing it over solid desiccants. The type of desiccants should be noted in that they must not have a reducing action in order to prevent a reaction with the oxygen content in the gas mixture. Non-reducing suitable desiccants are, for example, hygroscopic salts such as $CaCl_2$, $K_2CO_3$, $CuSO_4$, $MgClO_4$, $Na_2SO_4$, metal oxides such as BaO, CaO, MgO, acids such as $H_2SO_4$, acid anhydrides such as $P_2O_5$, molecular sieves or silica gel. Such desiccants are known to those skilled in the art or can be selected easily and are described, for example, in Römpps Chemie-Lexikon, 8th ed., p. 4370-4371 or in "Organikum", 21st ed., Wiley-VCH 2001, p. 24.

The various embodiments of the processes according to the invention in which the crude niobium alkoxide to be purified is treated with air or an oxygenous gas mixture may be preferred over treatment with alcohols owing to their more simple performability. Treatment with air or an oxygenous gas mixture can preferably be effected by means of passage through or passage over, but preferably by means of passage through, the liquid niobium alkoxide or else through a solution of the niobium alkoxide in a suitable solvent. When air or oxygenous gas mixture is only passed through the liquid or dissolved niobium alkoxide, which is possible but less preferred owing to the poorer, slower mixing, effective circulation of the niobium alkoxide, for example by stirring, has to be ensured.

Suitable solvents for the niobium alkoxides are, for example, aliphatic linear, branched or cyclic hydrocarbons such as n-pentane, n-hexane, n-heptane, isooctane, cyclohexane or aromatic hydrocarbons such as toluene or xylene, or mixtures of such solvents.

The inventive purifying operations with an alcohol $R^1OH$, air or other oxygenous gas mixtures are preferably performed in a temperature range of 10° C. to 70° C., preferably at 20° C. to 50° C., more preferably at room temperature (20-25° C.).

The required amount of dry air used for the purification can be determined readily via the progress of the color improvement of the niobium alkoxide. According to the degree of discoloration (Hazen color number) of the product to be purified, for air, a sufficient time for the passage through the niobium alkoxide is a time of 15 min to 2 h, often of 30 min to 1 h. For example, 0.1 to 10 ml/see, preferably 0.5 to 5 ml/sec, of air is passed through, corresponding to a total amount of 90 ml to 72 l, preferably 900 ml to 18 l, of air. These data should only be understood as a guideline; the values may—according to the purification requirement and discoloration present—also be higher or lower.

The oxygen content in protective gases such as argon which may be used in a mixture with added oxygen is guided by that of air. Readily usable mixtures then contain, for example, 2 to 35% by volume, preferably 5 to 25% by volume, of oxygen. A correspondingly suitable oxygen content can also be obtained by adding air, such that the protective gas present is an argon/nitrogen mixture or an argon-air mixture is used for the purification.

The purifying operations with an alcohol $R^1OH$, air or other oxygenous gas mixtures in the process according to the invention can optionally be followed by a distillation under reduced pressure. The performance of a distillation of niobium alkoxides under reduced pressure is known to those skilled in the art; see also D. C. Bradley, B. N. Chakravarti, W. Wardlaw; J. Chem. Soc. 1956, p. 2381-2384.

In the context of the invention, $C_2$-$C_5$-alkyl is, for example, ethyl, n-propyl, isopropyl, n-butyl, sec-butyl, tert-butyl, n-pentyl, 2-pentyl, 3-pentyl, 2-methylbutyl, 3-methylbutyl, neopentyl, 1,1-dimethylpropyl, 1,2-dimethylpropyl; in the context of the invention, $C_1$-$C_6$-alkyl is additionally, for example, methyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or 1-methyl-2-ethylpropyl; in the context of the invention, $C_1$-$C_{12}$-alkyl is additionally, for example, n-heptyl, n-octyl, n-nonyl, n-decyl and n-dodecyl.

Irrespective of the pretreatment and the technical previous history or of the preparation process of the niobium alkoxide starting materials in general, the processes according to the invention for purifying niobium alkoxides can achieve good successes.

However, it may be advantageous in various embodiments to use particularly low-halogen, preferably low-chloride, crude niobium alkoxides of the general formula (I) in the purification processes according to the invention. Suitable processes for preparing such low-halide, preferably low-chloride, crude niobium alkoxides are described, for example, in German patent application DE 10 2005 052 444.3.

Such processes for purifying niobium alkoxides of the general formula (I) include mixing crude niobium alkoxides having a halogen content, especially Cl content, of >100 ppm, in some cases >200 ppm, which contain, as an impurity, at least 0.05% by weight, preferably 0.1 to 10.0% by weight, of mono- or polynuclear halogen-containing metal alkoxides, with not more than 30% by weight, preferably 4 to 12% by weight, based on the total amount of the crude alkoxide, of an alcohol $R^2OH$ where $R^2$, independently of R and $R^1$, has one of the definitions specified above for R and $R^1$, and subsequently or simultaneously (for example after preceding dissolution in the alcohol $R^2OH$), metering in an excess of ammonia, based on the amount of mono- or polynuclear halogen-containing metal alkoxides, preferably of 0.1 to 5.0% by weight, based on the total amount of the crude alkoxide.

In various preferred embodiments of the invention, such a purification process, especially for eliminating halide, preferably chloride, impurities, can preferably be connected upstream of a process according to any of the previously described embodiments of the present invention. More preferably, such an upstream connected prior treatment with alcohol and ammonia can afford crude niobium alkoxide for use in a process according to the invention having a Cl content of less than 100 ppm by weight.

In preferred embodiments of the processes according to the invention, the crude niobium alkoxide used for purification is one having a Cl content of less than 100 ppm by weight (determined as chloride). The chloride content can, for example, be determined coulometrically to DIN 38405 D-1. Colorimetric methods are also suitable for orientation purposes, such as those based on the reaction with mercury(II) thiocyanate and subsequent reaction of the thiocyanate ions released with iron(I) ions to give red iron(III) thiocyanate. In the context of the present invention for purifying halide-containing, especially chloride-containing, niobium alkoxides, very particular preference is given to a combination of the process for reducing the halide content, preferably chloride content, and subsequent treatment with an alcohol $R^1OH$ or air or an oxygenous gas mixture.

The niobium alkoxides purified by the process according to the invention are virtually colorless or have only a slight pale yellow color to the naked eye. This color can be determined by means of measuring the Hazen color number. The process according to the invention preferably affords niobium alkoxides having a Hazen color number of <150, more preferably <120, most preferably <60. The Hazen color number (Pt—Co color number) is determined to DIN EN ISO 6271-1+2.

The present invention further provides the high-purity niobium alkoxides obtainable by the processes according to the invention.

Such high-purity niobium alkoxides prepared by the processes according to the invention are outstandingly suitable, for example, for the deposition of corresponding metal oxide layers by means of chemical vapor deposition (CVD) and are therefore valuable starting compounds for producing extremely robust components which find use, for example, in the electronics industry.

The invention will now be described in further detail with reference to the following non-limiting examples.

EXAMPLES

The Hazen color number (Pt—Co color number) was always determined to DIN EN ISO 6271-1+2.

Example 1

Inventive Purification of Niobium Ethoxide with Low Cl Content by Means of Addition of Ethanol a) Preparation of Niobium Ethoxide with Low Cl Content 810 g (3 mol) of niobium chloride were suspended in 600 ml of dry heptane. Within 2 h, 1 kg of absoluted (abs.) ethanol were metered thereto, in the course of which the internal temperature was kept below 40° C. by cooling with water/ice. The mixture was stirred at 25° C. for 1 h.

Thereafter, 321 g (19.5 mol) of ammonia were introduced at a maximum of 35° C. (cooling with water/ice) within 3 h. Thereafter, the mixture was filtered from the ammonium chloride, and ethanol was distilled off at 20 mbar, and finally under high vacuum at <1 mbar 70 g of abs. ethanol were added to the resulting crude ethoxide; subsequently, 33.8 g (1.99 mol) of ammonia were introduced at 23° C. within 1 h. After stirring at 23° C. for a further 2 h, 800 ml of hexane were added, the mixture was filtered and the ammonium chloride filtered off was washed with hexane. The combined hexane solutions were distilled under reduced pressure. The niobium ethoxide obtained after the hexane had been distilled off contained approx. 35 ppm of Cl.

b) Purification by Means of Addition of Ethanol 500 g of crude, undistilled niobium ethoxide from example 1a) with a Cl content of approx. 35 ppm and of orange-yellow color (Hazen color number>280) was admixed with 50 g of dry ethanol and heated to 50° C. with stirring for 2 h. Subsequently, the mixture was distilled at 150° C./0.5 mbar. The distillate had a yellowish color and a Hazen color number of 100; FIG. 1 shows the wavelength dependence of the absorption of this niobium ethoxide sample.

Example 2

Inventive Purification of Niobium Ethoxide by Means of Treatment with Air 1.7 kg of crude niobium ethoxide were distilled at 155° C./0.6 mbar and gave rise to an orange-yellow distillate (Hazen color number>280). Air dried over calcium chloride was passed through the distillate at 23° C. for 1 h. Thereafter, the product had a yellow color and a Hazen color number of 145.

Example 3

Inventive Purification of Niobium Ethoxide with Low Cl Content by Means of Treatment with Air Crude niobium ethoxide prepared analogously to example 1a) was distilled at 150° C./0.5 mbar. The orange-yellow niobium ethoxide distillate having a Cl content of 20 ppm was treated as in example 2 with air dried over $CaCl_2$ at 23° C. for 1 h. The color changed to light yellow.

Example 4

Figure 2:
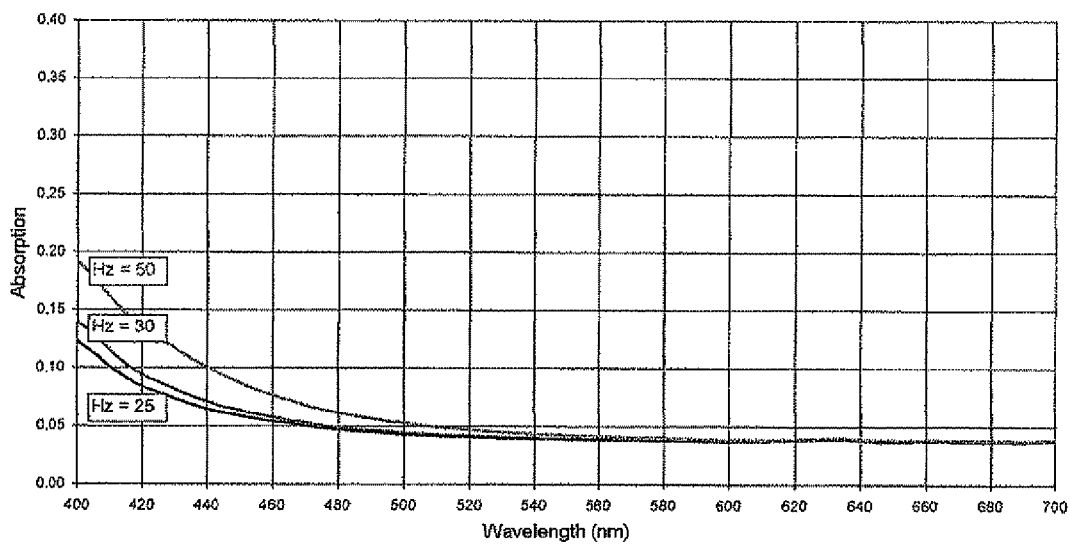
FIG. 2 is a graphical representation of the absorption of three niobium alkoxide samples prepared in accordance with a process according to another embodiment of the present invention, as a function of wavelength.

Inventive Purification of Niobium Ethoxide with Low Cl Content by Means of Treatment with Air a) Preparation of Niobium Ethoxide with Low Cl Content.
11.557 kg of crude niobium ethoxide prepared according to 1a) were treated with 1156 g of ethanol and 57.8 g of $NH_3$, likewise as in 1a), to lower the Cl value. The resulting crude niobium ethoxide subsequently had a Cl content of 35 ppm. The product was distilled in three portions at 150° C./0.5 mbar.

b) Purification by Means of Treatment with Air
Air dried over $CaCl_2$ was passed through 2 kg in each case of the three different distillates from 4a) at a rate of approx. 50 ml/min, in each case for ½ h. The subsequent measurement of the Hazen color number of the three niobium ethoxide portions gave values of 25, 30 and 50. The wavelength dependence is shown in FIG. 2.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A process comprising: (a) providing a crude niobium alkoxide starting material comprising at least one compound of the general formula (I)

$$Nb(OR)_5 \hspace{2cm} (I)$$

wherein each R independently represents a linear or branched $C_{1-12}$ alkyl group; and (b) contacting the crude niobium alkoxide starting material with a treatment medium comprising a component selected from the group consisting of (i) one or more alcohols of the general formula (II) in an amount of 0.01 to 5% by weight, (ii) air or an oxygen-containing gas, and (iii) combinations thereof;

$$R^1OH \hspace{2cm} (II)$$

wherein each $R^1$ independently represents a linear or branched $C_{1-12}$ alkyl group.

2. The process according to claim 1, further comprising distilling the crude niobium alkoxide starting material subsequent to contacting with the treatment medium.

3. The process according to claim 1, wherein each R independently represents a linear or branched $C_{1-6}$ alkyl group.

4. The process according to claim 1, wherein each R represents an identical linear or branched $C_{1-6}$ alkyl group.

5. The process according to claim 1, wherein each R represents an ethyl group.

6. The process according to claim 1, wherein the treatment medium comprises an alcohol of the general formula (II) and wherein $R^1$ represents a linear or branched $C_{1-6}$ alkyl group.

7. The process according to claim 1, wherein the treatment medium comprises an alcohol of the general formula (II) and wherein $R^1$ represents an ethyl group.

8. The process according to claim 5, wherein the treatment medium comprises an alcohol of the general formula (II) and wherein $R^1$ represents an ethyl group.

9. The process according to claim 1, wherein the treatment medium comprises dry air or a dry oxygen-containing gas.

10. The process according to claim 1, wherein the crude niobium alkoxide starting material has a halogen content of less than 100 ppm by weight.

11. The process according to claim 1, wherein providing the crude niobium alkoxide starting material comprises: (i) providing an initial niobium alkoxide material having a halogen content of greater than 100 ppm, wherein the halogen content comprises a mono- or polynuclear halogen-containing metal alkoxide; (ii) mixing the initial niobium alkoxide material with not more than 30% by weight, based on the total amount of the initial alkoxide material, of an alcohol $R^2OH$ where $R^2$ independently represents a linear or branched $C_{1-12}$ alkyl group; and (iii) subsequently or simultaneously, adding an excess of ammonia to the mixed initial material and alcohol, the excess based on the mono- or polynuclear halogen-containing metal alkoxide.

12. The process according to claim 8, wherein providing the crude niobium alkoxide staffing material comprises: (i) providing an initial niobium alkoxide material having a halogen content of greater than 100 ppm, wherein the halogen content comprises a mono- or polynuclear halogen-containing metal alkoxide; (ii) mixing the initial niobium alkoxide material with not more than 30% by weight, based on the total amount of the initial alkoxide material, of an alcohol $R^2OH$ where $R^2$ independently represents a linear or branched $C_{1-12}$ alkyl group; and (iii) subsequently or simultaneously, adding an excess of ammonia to the mixed initial material and alcohol, the excess based on the mono- or polynuclear halogen-containing metal alkoxide.

13. The process according to claim 11, wherein the alcohol $R^2OH$ is mixed with the initial niobium alkoxide material in an amount of 4 to 12% by weight.

14. The process according to claim 11, wherein the initial niobium alkoxide material has a halogen content of greater than 200 ppm.

15. The process according to claim 1, wherein the crude niobium alkoxide starting material is contacted with one or more alcohols of the general formula (II) in an amount of 0.01 to 5% by weight and air or an oxygen-containing gas.

* * * * *

UNITED STATES PATENT AND TRADEMARK OFFICE
CERTIFICATE OF CORRECTION

PATENT NO. : 7,566,796 B2  Page 1 of 1
APPLICATION NO. : 11/855219
DATED : July 28, 2009
INVENTOR(S) : Knud Reuter It is certified that error appears in the above-identified patent and that said Letters Patent is hereby corrected as shown below:

Col. 8, in Claim 12, line 44, delete "staffing" and insert --starting--.

Signed and Sealed this

Eighth Day of September, 2009

David J. Kappos
*Director of the United States Patent and Trademark Office*